United States Patent [19]

Wong

[11] Patent Number: 4,756,622
[45] Date of Patent: Jul. 12, 1988

[54] COMPACT APPARATUS FOR MEASURING ABSORPTION BY A GAS

[75] Inventor: Jacob Y. Wong, Santa Barbara, Calif.

[73] Assignee: Hibshman Corporation, San Luis Obispo, Calif.

[21] Appl. No.: 863,314

[22] Filed: May 15, 1986

[51] Int. Cl.[4] ............ G01N 21/01; G01N 21/59
[52] U.S. Cl. ............................. 356/437; 356/436
[58] Field of Search ............ 356/350, 436–441, 356/437

[56] References Cited

U.S. PATENT DOCUMENTS 4,305,046 12/1981 Le Floch et al. ............ 356/350

FOREIGN PATENT DOCUMENTS 8203503 10/1982 World Int. Prop. O. .

Primary Examiner—R. A. Rosenberger
Assistant Examiner—Steve McGowan
Attorney, Agent, or Firm—Daniel C. McKown

[57] ABSTRACT

The measurement of weak absorption lines is facilitated by the use of a long transmission path length, which is difficult to obtain in compact or portable instruments. In the present invention, light is made to travel through a limited volume of gas thousands of times. The light is placed on a closed optical path on which it circulates through the gas sample. After a desired number of passes through the gas sample, the light is removed from the closed optical path. Introduction of the light to the closed optical path and removal therefrom is accomplished through the use of a polarizing beamsplitter and a pockels cell located on the closed path. Light is put onto the closed path by the polarizing beamsplitter which imparts a specific polarization. During the first circuit the pockels cell alters the polarization by 90 degrees thereby preventing the light from escaping back out through the polarizing beamsplitter. After the desired number of circuits, the pockels cell again alters the polarization by 90 degrees thereby permitting the light to be redirected out of the closed path by the polarizing beamsplitter.

9 Claims, 4 Drawing Sheets

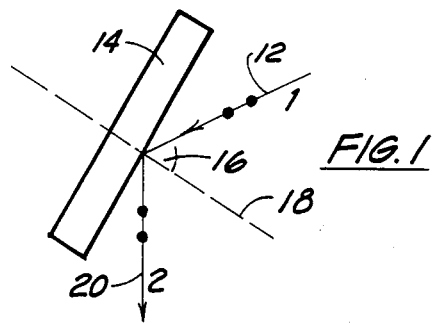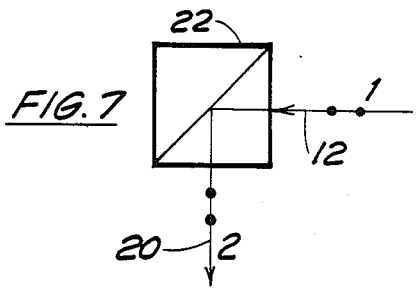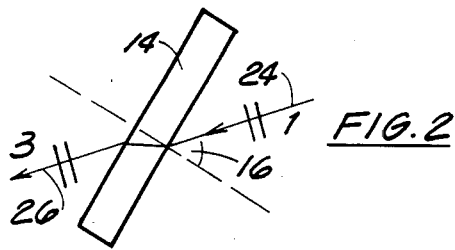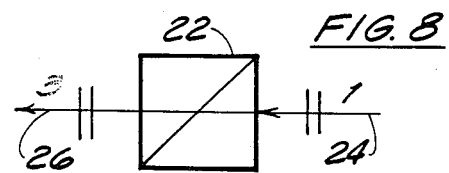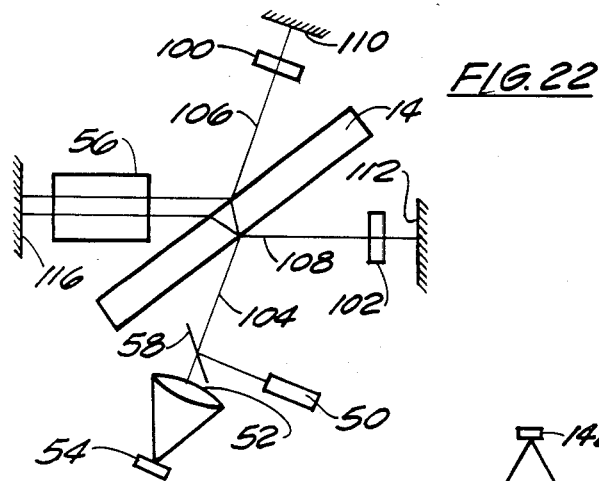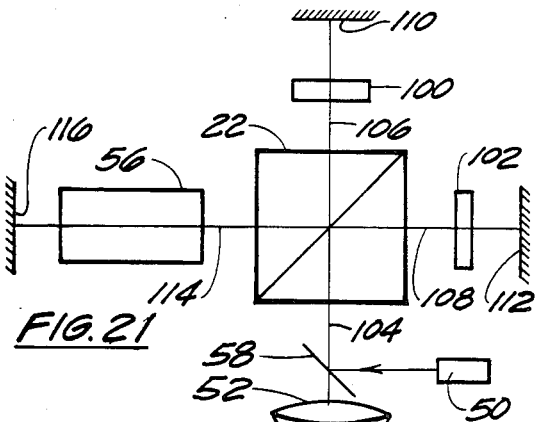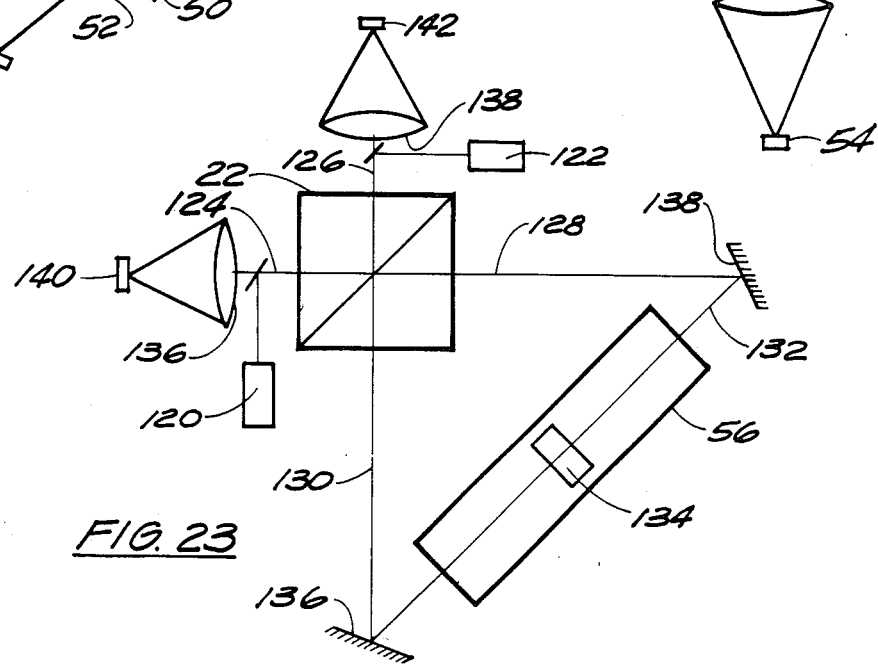

COMPACT APPARATUS FOR MEASURING ABSORPTION BY A GAS

BACKGROUND OF THE INVENTION

1. Field of the Invention

The present invention is in the field of gas analysis and more particularly relates to a compact apparatus for measuring the absorption of light or other radiation by a gas that absorbs only weakly.

2. The Prior Art

Certain gases have absorption bands that absorb so weakly that absorption can only be detected after the radiation has traveled a relatively long distance, perhaps kilometers, through the gas. On the other hand, practical gas analyzers for commercial use, as opposed to laboratory apparatus, typically are small enough to be portable, and are definitely too small to provide path lengths thousands of meters long.

Furthermore, the amount of gas available might be insufficient to fill a sample chamber large enough to provide the necessary path lengths.

It is well-known to use mirrors to fold an optical beam so that the beam can traverse the sample cell a number of times. Although the present invention makes use of a folded optical path, that alone is not the inventive step.

A multi-path absorption cell was described by J. U. White, Journal of the Optical Society of America, Volume 32, page 285 (1942). The essential parts of the White cell consist of three spherical concave mirrors all having the same radius of curvature, and positioned to form an optical cavity. Utilizing the principle outlined in White's article, at least two companies have marketed a ten-meter multi-path cell, and one of the companies has also marketed a forty-meter multi-path cell.

The number of times the light can be passed through a White cell is limited by the spherical aberation of the mirrors. Thus, the White cell is not compatible with the present invention in which the light may be passed through the sample cell thousands of times.

SUMMARY OF THE INVENTION

A major purpose of the present invention is to provide a closed optical path on which radiation can travel repeatedly, and at least part of which path extends through a space in which a gas sample is present, so that the radiation can travel a long distance through the gas in spite of the fact that the physical dimensions of the apparatus are relatively small.

Another major purpose of the present invention is to provide means for introducing radiation into a closed optical path and, at a later time, for removing the radiation from the closed optical path.

As used herein, the word radiation refers to electromagnetic radiation without limitation as to its wavelength; however, the most interesting applications presently contemplated make use of radiation in the infrared, visible, and ultraviolet portions of the spectrum. Also, as used herein, the word path refers to a line segment or series of line segments along which radiation travels. A closed path is defined to be a path which returns to an initial starting point and direction.

In accordance with the present invention, radiation is directed into a closed path on which it travels repetiively thousands of times through a sample of gas whose absorption is to be measured. This yields the equivalent of a path length through the gas of several thousand meters, typically. At some point in time, the radiation is redirected out of the closed path and applied to a detector that permits the intensity of the recovered radiation to be measured. The intensity is similarly measured again but without the sample of gas in the optical path. Comparison of the two intensities permits the absorption caused by the gas to be determined.

The novel features which are believed to be characteristic of the invention, both as to organization and method of operation, together with further objects and advantages thereof, will be better understood from the following description considered in connection with the accompanying drawings in which several preferred embodiments of the invention are illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is an optical diagram showing an s-polarized ray reflected from a dielectric surface;

FIG. 2 is an optical diagram showing a p-polarized ray transmitted through a dielectric plate;

FIG. 7 is an optical diagram showing an s-polarized ray reflected by a polarizing beamsplitter cube;

FIG. 8 is an optical diagram showing a p-polarized ray transmitted through a polarizing beamsplitter cube;

FIG. 21 is an optical diagram showing the path of a ray as it passes through another embodiment of the present invention;

FIG. 22 is an optical diagram showing the path of a ray as it passes through a variation of the embodiment of FIG. 21; and, FIG. 23 is an optical diagram showing the path of a ray as it passes through another embodiment of the present invention.

DETAILED DESCRIPTION OF THE PREFERRED EMBODIMENTS

Figure 3:
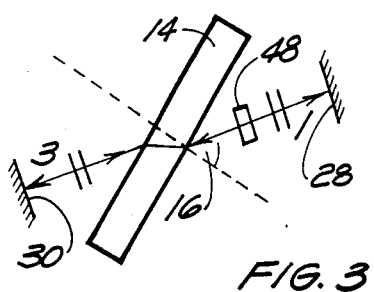
FIG. 3 is an optical diagram showing mirrors interposed in the path of a p-polarized ray to provide a closed path.

The present invention makes use of the properties of polarized radiation, and a brief review of those properties as they apply to the present invention will be given.

It will be recalled that electromagnetic waves vibrate in a direction transverse to the direction the wave is moving, and unpolarized light is considered to contain components vibrating in all possible planes that contain the ray. Radiation that vibrates in only one plane is said to be plane-polarized or, as used herein, linearly polarized.

FIG. 1 shows a ray 12 on path 1 incident upon a plate 14 of dielectric material at the polarizing angle 16. The dots on the ray 12 indicate that the vibrations are in a plane perpendicular to the plane of incidence. The plane of incidence is defined as a plane containing both the normal 18 to the surface of the plate 14 as well as the incident ray 12. In FIG. 1, the plane of incidence coincides with the plane of the page, and the vibrations are perpendicular to the page. Because the vibrations are perpendicular to the plane of incidence, the ray 12 is referred to as s-polarized. When as s-polarized ray is incident at the (Brewster's) polarizing angle 16, the entire ray is reflected along a path 2 as indicated by the ray 20 of FIG. 1. Following conventional notation, an s-polarized ray is denoted by dots, while a p-polarized ray, in which all of the vibrations are in the plane of incidence is denoted by a series of lines transverse to the ray.

A similar result is shown in FIG. 7 where a polarizing beamsplitter cube 22 is used in place of the plate 14 of dielectric material. Both the plate 14 and the cube 22 are but examples of a class of devices that are referred to herein by the generic term "polarizing beamsplitter." When the polarizing beamsplitter cube 22 is used, the path 2 is perpendicular to the path 1. In FIG. 2, by way of contrast, when a p-polarized ray 24 is incident upon the plate 14 of dielectric material at the polarizing angle 16, the entire ray passes through the dielectric material and emerges on path 3, as indicated by the ray 26.

The comparable situation for the polarizing beamsplitter cube is shown in the diagram of FIG. 8. It is a property of such a cube that the transmitted ray 26 has substantially the same direction as the incident ray 24.

Comparison of FIGS. 1 and 2 shows that the direction of polarization of the incident ray determines the direction of the reflected or transmitted ray. If the incident ray on path 1 is s-polarized, the reflected ray 20, on path 2, will also be s-polarized. But if the incident ray 24 on path 1 is p-polarized, the transmitted ray 26 on path 3 will also be p-polarized. The direction of polarization of the incident ray determines whether the ray exits on path 2 or on path 3. The same applies when the polarizing beamsplitter cube 22 is used, as seen by comparison of FIGS. 7 and 8.

In FIG. 3 a closed path for the p-polarized rays is formed by interposing the plane mirrors 28 and 30 in path 1 and path 3. As the arrows on the rays indicate, any p-polarized radiation that coincides with any part of the path will repetitively traverse the space between the mirrors 28, 30.

Figure 9:
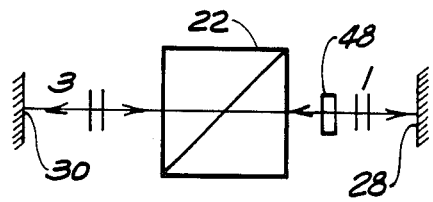
FIG. 9 is an optical diagram showing mirrors interposed in the path of a p-polarized ray to provide a closed path.

A similar closed path for the p-polarized rays on paths 1 and 3 is evident where the polarizing beamsplitter cube 22 is used, as shown in FIG. 9.

Figure 4:
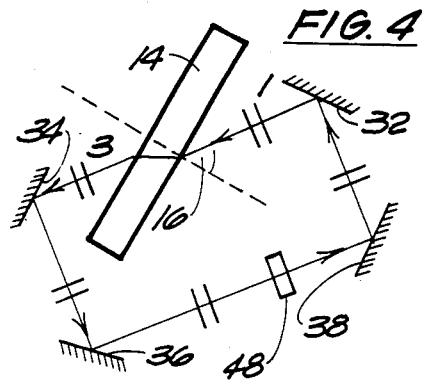
FIG. 4 is an optical diagram showing an alternative way of interposing mirrors in the path of a p-polarized ray to provide a closed path.
Figure 10:
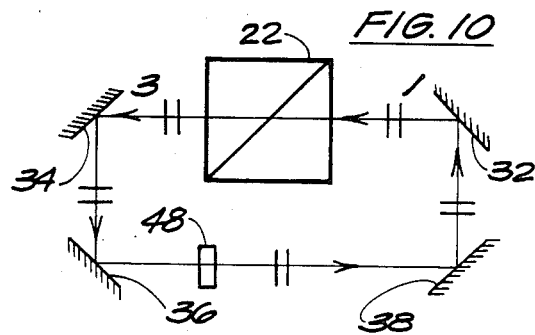
FIG. 10 is an optical diagram showing an alternative way of interposing mirrors in the path of a p-polarized ray to provide a closed path.

FIG. 4 shows another way of producing a closed path for the p-polarized radiation. In the arrangement of FIG. 4, four mirrors 32, 34, 36 and 38 are used, and they are positioned and oriented in such a way that the radiation circulates on the closed path shown.

Note that if the light that is traveling on the closed paths of FIGS. 3, 4, 9, and 10 were suddenly to have its polarization changed from p to s, the radiation would be deflected from the closed path and onto the path 2, as indicated in FIGS. 1 and 7.

Figure 5:
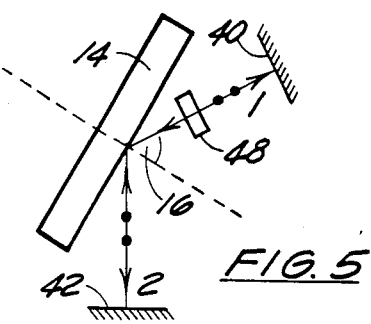
FIG. 5 is an optical diagram showing mirrors interposed in the path of an s-polarized ray to provide a closed path.

FIG. 5 is somewhat similar to FIG. 3 except that s-polarized radiation is used. The mirrors 40, 42 are interposed perpendicular to path 1 and path 2, respectively, to produce a closed path on which the radiation travels repeatedly.

Figure 11:
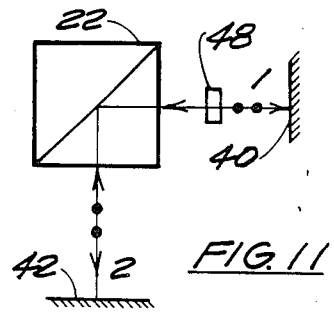
FIG. 11 is an optical diagram showing mirrors interposed in the path of an s-polarized ray to provide a closed path.

FIG. 11 shows the analogous paths for the polarizing beamsplitter cube 22.

Figure 6:
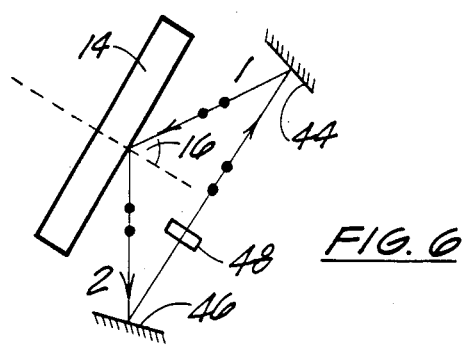
FIG. 6 is an optical diagram showing an alternative way of interposing mirrors in the path of an s-polarized ray to provide a closed path.

FIG. 6 shows mirrors 44, 46 interposed in the paths 1 and 2 to produce a different shaped closed path than that shown in FIG. 5.

Figure 12:
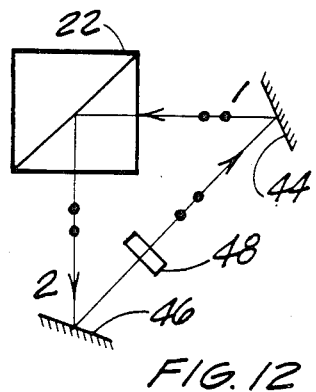
FIG. 12 is an optical diagram showing an alternative way of interposing mirrors in the path of an s-polarized ray to provide a closed path.

FIG. 12 shows the analogous situation for the polarizing beamsplitter cube 22.

It should be noted that the closed paths of FIGS. 5, 6, 11, and 12 coincide, at least in part, with the paths 1 and 2.

If the polarization of the radiation traveling the closed paths shown in FIGS. 5, 6, 11, and 12 were to be altered suddenly from s to p, the radiation would thereafter be removed from the closed path by way of the path 3, as indicated in FIGS. 2 and 8.

Thus, it has been shown in FIGS. 1-12 that polarized radiation traveling a closed path can be removed from that closed path by altering its direction of polarization by 90°. The present inventor completed his combination by interposing a pockels cell 48 in the closed path.

It is well-known that when no voltage is applied to a pockels cell, the direction of polarization of the radiation passing through it will not be altered. However, when a voltage is applied to the pockels cell, the polarization of the radiation will be rotated through an angle that depends on the magnitude of the applied voltage.

In accordance with a preferred embodiment of the present invention, the pockels cell 48 can be located at any point in the closed paths of FIGS. 3, 4, 5, 6, 9, 10, 11, and 12. In the embodiments of FIGS. 4, 6, 10, and 12, the radiation circulates in a particular sense around the closed path, and at some point in time, a sufficient voltage is applied to the pockels cell to cause a rotation of the direction of polarization by 90°.

The transmissivity of a pockels cell can be extremely high—on the order of 99.99%. Therefore, even though the radiation passes through the pockels cell many times, little loss of radiation occurs.

In the embodiments of FIGS. 3, 5, 9, and 11, the radiation travels back and forth along each particular segment of the closed path, and the radiation will pass twice through the pockels cell before being incident on the dielectric plate 14 or the polarizing beamsplitter cube 22. Accordingly, in the arrangements of FIGS. 3, 5, 9, and 11, the voltage applied to the pockels cell 48 should produce a change in the direction of polarization of 45° on each pass through the pockels cell. The pockels cell still produces a total change in the direction of polarization of 90°, but that change is produced in two steps.

FIGS. 13-23 show specific embodiments in which the above-described techniques are applied to the measurement of the absorption of radiation by a sample of gas or liquid.

In all of the following embodiments, the radiation originates in a source 50. Since spreading of the beam is one of the limiting factors in the use of the present invention, it is highly desirable that the source 50 produce a beam of radiation having the smallest practical divergence. To this end, in a preferred embodiment the source 50 includes a laser diode and a collimating optical system. As will be discussed below, such a source is capable of producing a beam of such small divergence that extremely long path lengths, on the order of kilometers, can be obtained in a relatively compact apparatus.

Also present in the embodiments shown in FIGS. 3-23 is apparatus for collecting and detecting the radiation that has passed repeatedly through the sample of gas. In the drawings, this apparatus is shown as including a collecting lens 52 that presents a large enough aperture to collect the emerging beam of radiation and to concentrate it on a detector cell 54. In the preferred embodiment, a lens is used, and the detector cell 54 consists of a silicon photodiode.

The pockels cell 48 used in the embodiments of FIGS. 13-20 is of a well-known type in which no rotation of the plane of polarization occurs unless and until a voltage is applied across the pockels cell. The magnitude of the applied voltage determines the amount of rotation of the plane of polarization produced as the radiation passes through the pockels cell. The application of voltage pulses to the pockels cell 48 is controlled by the programmable pulse generator and timer 49 of FIGS. 13-20, which permits a chosen sequence of voltage pulses of selected magnitudes to be applied to the pockels cell 48.

Also shown in each of the embodiments of FIGS. 13-23 is a volume of gas 56 located on the closed optical path that the radiation repeatedly travels. From the standpoint of operation of the invention, it is immaterial whether the gas is totally enclosed in a container, is partially enclosed in an airway through which the gas may flow, or whether the gas is unconfined. As noted above, it is also immaterial whether the sample consists of a gas, a vapor, or a liquid, or combinations thereof. However, for convenience of the discussion, the sample will be assumed to consist of a gas.

In the embodiments of FIGS. 13-22 the sample 56 could be contained in an optical device, exemplified by a White cell, in which the radiation undergoes multiple reflections. This has the advantages of causing a greater dwell time in that portion of the optical path and of greatly increasing the distance the radiation travels through the sample.

In the embodiments of FIGS. 13, 15, 17, 19, and 21-23, it is desirable to make use of a mirror 58 for directing the radiation from the source 50 onto a particular path. This is done to prevent physical interference between the radiation source 50 and the collector which consists of the lens 52 and the detector cell 54. The mirror 58, in a preferred embodiment is partially reflective and partially transmissive, and its diameter may be as large as that of the lens 52. In an alternative embodiment in which the beam of radiation emerging from the source 50 is small in diameter compared to the diameter of the lens 52, the mirror 58 is entirely reflective, but of a size that is considerably smaller than the diameter of the lens 52, whereby the mirror 58 does not block a substantial part of the area of the lens 52.

In the following paragraphs, the embodiments of FIGS. 13-23 will be described in detail.

Figure 13:
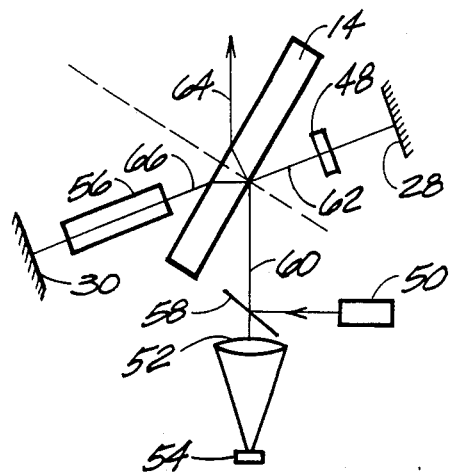
FIG. 13 is an optical diagram showing the path of a ray as it passes through a first preferred embodiment of the apparatus of the present invention.

In FIG. 13, unpolarized radiation from the source 50 is directed by the mirror 58 onto the path 60. As with all of the drawings, the paths show the direction of the centerline of a collimated beam. As in all of the drawings, the path 60 is incident on the beamsplitter at the polarizing angle. Accordingly, the s-polarized component is reflected on the path 62, while the p-polarized component is transmitted through the dielectric plate 14 and emerges on the path 64. The s-polarized component on the path 62 passes through the pockels cell 48 which rotates its direction of polarization by 45 degrees in response to an applied electrical signal (a constant voltage). The beam continues to the mirror 28 which reverses its direction. Upon passing through the pockels cell 48 a second time, the direction of polarization is again rotated 45 degrees, so that the radiation that has passed through the pockels cell 48 a second time is p-polarized. This radiation on the path 62 impinges on the plate 14 of dielectric material and is transmitted through that material and emerges on the path 66. This radiation next passes through the volume 56 of gas and is turned back upon itself by the mirror 30. Since the radiation still has the p-polarization, it is transmitted through the plate 14 again and emerges on the path 62. In the best known mode of operating the invention, the applied voltage is removed from the pockels cell 48, which causes the pockels cell to pass the radiation without changing its direction of polarization. In this manner, the radiation is trapped on the paths 62, 66 and passes through the volume 56 of gas numerous times.

At some point in time, the voltage is again applied to the pockels cell 48 which causes it to again alter the direction of polarization of the radiation passing through it. Assuming the radiation has just emerged from the plate 14 and is heading on the path 62 towards the mirror 28, the pockels cell 48 alters its direction of polarization 45 degrees on each pass through the pockels cell, so that as the radiation again approaches the plate 14, it has become s-polarized. Therefore, the radiation is not transmitted by the plate 14, but instead is reflected on the path 60, where it passes through the partially reflective mirror 58 and where it is collected by the lens 52 and concentrated onto the detector 54. As is well known in the art, the detector 54 produces an electrical signal that is related to the intensity of the radiation falling on the detector cell 54. In a preferred embodiment, the magnitude of the signal produced when a gas is present in the volume 56 is compared to the magnitude of the signal produced when the gas being analyzed is not present in the volume 56, and the reduction in the signal when the gas is present is attributed to absorption of the radiation by the gas. The effective distance the radiation has travelled through the gas is equal to the length of the volume of gas in the direction of the path 66 and the number of times the radiation passes through that volume while it is on the repetitive closed path. This number may be determined by taking into account the time interval that elapses between when the voltage is removed from the pockels cell and when the voltage is again applied to the pockels cell, taking into account the fact that the radiation travels approximately 30 centimeters per nanosecond.

Figure 17:
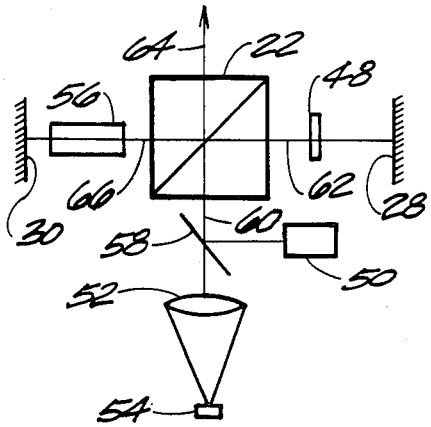
FIG. 17 is an optical diagram showing the path of a ray as it passes through a variation of the embodiment of FIG. 13.

The operation of the embodiment of FIG. 17 is identical to that of FIG. 13, the difference being that some of the angles are different when a polarizing beamsplitter cube 22 is used in place of the plate 14.

Figure 14:
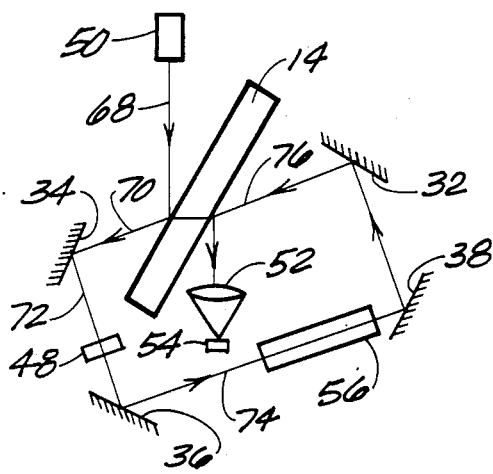
FIG. 14 is an optical diagram showing the path of a beam of radiation as it passes through a second preferred embodiment of the apparatus of the present invention.

In the embodiment of FIG. 14, radiation from the source 50 travels on the path 68 and impinges on the plate 14 at the polarizing angle. The s-polarized component is refelected on the path 70 and redirected by the mirror 34 to the path 72 which takes it through the pockels cell 48. At this point in time, a first signal consisting of a constant voltage is being applied to the pockels cell that causes it to rotate the direction of polarization through an angle of 90 degrees, so that the radiation emerging from the pockels cell 48 is p-polarized. That radiation is redirected onto the path 74 by the mirror 36. The path 74 takes the radiation through the volume 56 of gas. Thereafter, the radiation is redirected by the mirrors 38 and 32 so that the p-polarized radiation on the path 76 impinges at the polarizing angle on the plate 14. The plate 14 transmits the p-polarized radiation, and the mirror 32 is so located that the radiation emerges from the plate 14 on the path 70. Before the radiation can again reach the pockels cell 48, a second signal, consisting of zero voltage, is applied to the pockels cell thereby to prevent the pockels cell from altering the polarization of the beam. Accordingly, the p-polarized beam circulates around the closed path, passing each time through the volume 56 of gas. After a particular amount of time has passed, the first signal is again applied to the pockels cell 48, and as the radiation passes through it, the polarization of the radiation is changed from p to s. The s-polarized radiation then continues on the paths 74 and 76, but on striking the plate 14 is not transmitted, but instead is reflected at the critical angle into the lens 52 which focuses it onto the detector cell 54.

Figure 18:
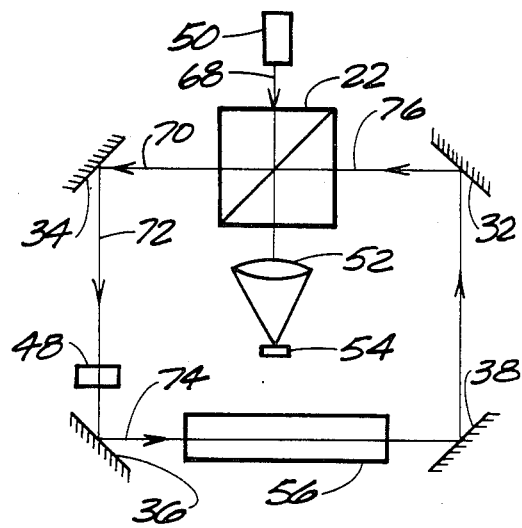
FIG. 18 is an optical diagram showing the path of a ray as it passes through a variation of the embodiment of FIG. 14.

The operation of the embodiment of FIG. 18 is the same as that of the embodiment of FIG. 14. In both FIG. 14 and FIG. 18, it is possible that some of the radiation emitted by the source 50 will pass through the beamsplitter and into the lens 52. If this becomes a problem, the unwanted radiation can be gated out since its time of arrival at the detector 54 identifies it as not having circulated on the closed path.

In the embodiments shown in FIGS. 13, 14, 17, and 18, the radiation on the repetitive closed path was p-polarized. In contrast, in the embodiments shown in FIGS. 15, 16, 19, and 20, the radiation that is traveling repeatedly on the closed path is s-polarized.

Figure 15:
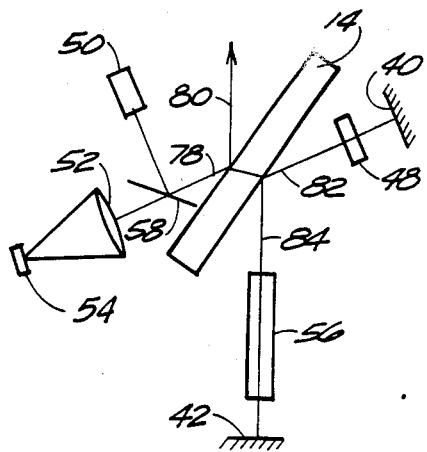
FIG. 15 is an optical diagram showing the path of a ray as it passes through a third preferred embodiment of the apparatus of the present invention.

In the embodiment of FIG. 15, unpolarized radiation from the source 50 is redirected by the mirror 58 onto the path 78 which impinges on the plate 14 at the polarizing angle. The s-polarized component is reflected on the path 80, while the p-polarized component is transmitted by the plate 14 and emerges on the path 82. The p-polarized component then continues on the path 82 through the pockels cell 48 to the mirror 40 which reverses its direction and sends it back through the pockels cell 48. During this time, a first signal is applied to the pockels cell 48 that causes it to rotate the direction of polarization by 45 degrees on each of the two passes, so that following the second passage through the pockels cell 48, the radiation is s-polarized. Because the radiation is s-polarized, and because it is incident at the polarizing angle, the radiation is reflected from the plate 14 and proceeds along the path 84. This path takes the radiation through the volume 56 of gas, to the mirror 42, and back through the volume 56 of gas. At this point in time, a second signal is applied to the pockels cell 48 which causes the pockels cell to pass the radiation without affecting its direction of polarization. Therefore, the radiation travels repeatedly along the paths 82 and 84, until a desired number of passages have been made. Then a first signal is applied to the pockels cell 48 which causes the pockels cell to rotate the direction of polarization by 45 degrees on each passage through it. The radiation is thereby given a p-polarization which causes it to be transmitted through the plate 14 to emerge on the path 78, to pass through the partially reflecting mirror 58 and the lens 52 and to be concentrated upon the detector cell 54. Note that the radiation was s-polarized while it travelled repeatedly on the paths 82, 84.

Figure 19:
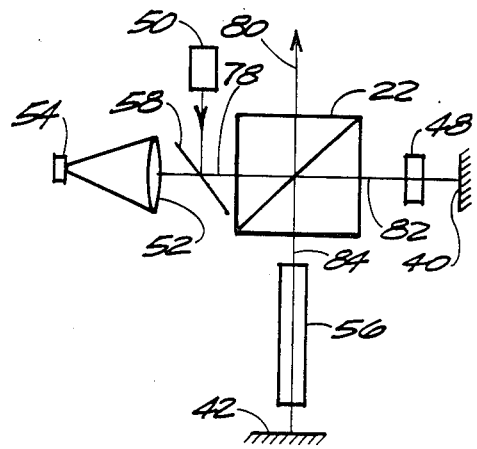
FIG. 19 is an optical diagram showing the path of a ray as it passes through a variation of the embodiment of FIG. 15.

The operation of the embodiment of FIG. 19 is the same as that of the embodiment of FIG. 15.

Figure 16:
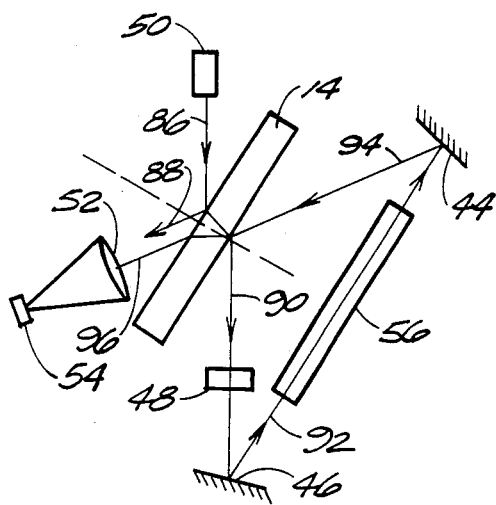
FIG. 16 is an optical diagram showing the path of a ray as it passes through a fourth preferred embodiment of the apparatus of the present invention.

In the embodiment of FIG. 16, unpolarized radiation from the source 50 travels on the path 86 and impinges on the plate 14. The s-polarized component is reflected on the path 88, while the p-polarized component is transmitted through the plate 14 and emerges on the path 90. The mirrors 44, 46 are arranged to bring the radiation back to the point at which it emerged from the plate 14. The p-polarized radiation on the path 90 encounters the pockels cell 48. A first signal is being applied to the pockels cell 48 to cause it to rotate the direction of polarization of the radiation through 90 degrees, so that the radiation that emerges from the pockels cell 48 is s-polarized. That radiation is then reflected from the mirror 46 along the path 92 which passes through the volume 56 of gas. Thereafter, the mirror 44 directs the radiation along the beam 94, and because the radiation is s-polarized, it is reflected from the plate 14 along the path 90. At this point in time, a second signal is applied to the pockels cell 48 that causes it to permit the radiation to pass through it without change in the direction of polarization. In this manner, s-polarized radiation circulates a large number of times on a closed path consisting of the segments 90, 92, and 94. After the desired number of circuits have been completed, the first signal is again applied to the pockels cell 48 causing it to alter the direction of polarization by 90 degrees, so that the radiation emerging from the pockels cell is p-polarized. This radiation then travels on the paths 92 and 94, and passes through the plate 14, emerging on the path 96. The radiation on the path 96 is collected by the lens 52 and concentrated onto the detector cell 54.

Figure 20:
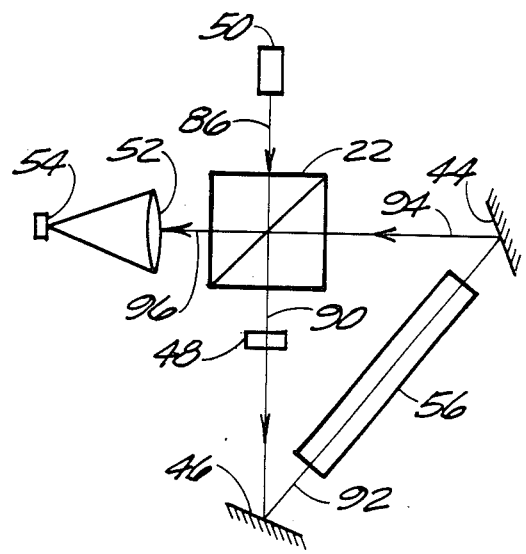
FIG. 20 is an optical diagram showing the path of a ray as it passes through a variation of the embodiment of FIG. 16.

The operation of the embodiment shown in FIG. 20 is identical to that of the embodiment of FIG. 16.

The embodiments of FIGS. 21–23 are remarkable in that both the p and s polarized components are caused to travel a closed course repetitively and simultaneously.

Turning to the embodiment of FIG. 21, it will be noted that two pockels cells 100, 102 are used. Unpolarized radiation from the source 50 is directed by the partially-reflective mirror 58 onto the path 104. The p-polarized component is transmitted through the cube 22 on the path 106, while the s-polarized component is reflected on the path 108. A first signal is applied to the pockels cells 100, 102 causing each of them to rotate the direction of polarization of any radiation passing through them by 45 degrees. The p-polarized component on the path 106 passes through the pockels cell 100, is reflected back on itself by the mirror 110 and passes a second time through the pockels cell 100 thereby being converted to s polarization. Simultaneously, the s-polarized radiation on the path 108 passes through the pockels cell 102 and is turned back upon itself by the mirror 112, and after passing through the pockels cell 102 a second time has acquired a p polarization. Accordingly, the s-polarized radiation travelling toward the cube 22 on the path 106 is reflected by the cube onto the path 114, while the p-polarized radiation approaching the cube on the path 108 is transmitted through the cube 22 and emerges on the path 114. Thus, both a p-polarized component and a s-polarzied component travel along the path 114, through the volume 56 of gas and are reflected back upon themselves by the mirror 116.

Upon interacting with the cube 22 again, the s-polarized component on the path 114 is reflected onto the path 106, while the p-polarized component on the path 114 is transmitted on the path 108. By this time, a second signal has been applied to the pockels cells 100, 102 which causes them to pass radiation without affecting the direction of polarization. In this manner, the s-polarized component is trapped and travels repeatedly on the paths 106, 114, while the p-polarized component is trapped and repeatedly travels the paths 108 and 114. After a desired number of passage have been made, the first signal is applied again to the pockels cells 100, 102, thereby altering the direction of polarization of the radiation passing through them, so that the s-polarized radiation on the path 106 is converted to p-polarized radiation and is transmitted by the cube 22 on the path 104 while the p-polarized radiation on the path 108 is converted to s-polarized radiation and is reflected by the cube 22 onto the path 104. Both components on the path 104 pass through the partially-transmissive mirror 58 and are collected by the lens 52 which concentrates them onto the detector cell 54.

The operation of the embodiment of FIG. 22 is identical to that of the embodiment of FIG. 21.

The embodiment shown in FIG. 23 is rather unique in that two s-polarized beams of radiation circulate in opposite senses around a closed path that includes a volume 56 of gas.

Unpolarized radiation from the source 120, 122 is reflected by partially-reflective mirrors onto the paths 124, 126. The s-polarized components are reflected by the cube 22 onto the paths 126, 124 respectively and are wasted. The p-polarized components are transmitted by the cube 22 and emerge on the paths 128, 130 respectively. Through the use of the mirrors 136, 138, these p-polarized components are redirected onto the path 132 which they travel in opposite directions. At some point, a first signal is applied to the pockels cell 134 which causes it to rotate the direction of polarization of radiation passing through it by 90 degrees. Accordingly, both of the p-polarized components become s-polarized. Thereafter, a second signal is applied to the pockels cell 134 which causes it to pass radiation without altering the direction of polarization of that radiation. Accordingly, the s-polarized components circulate around the closed path defined by the segments 128, 130, 132 a great number of times and in opposite senses. Thereafter, the first signal is again applied to the pockels cell 134, and this causes the s-polarized components to become p-polarized. Thereupon the component approaching the cube 22 on the path 128 is transmitted through the cube and emerges on the path 124, to be collected by the lens 136 and concentrated on the detector 140. Likewise, the p-polarized component approaching the cube 22 on the path 130 is transmitted by the cube and emerges on the path 126, to be collected by the lens 138 and concentrated onto the detector cell 142.

Thus, a number of embodiments have been shown of a compact apparatus for use in measuring the absorption of a gas. Common to all of these embodiments is the use of a pockels cell and a polarizing beamsplitter to permit radiation from a source to be placed on a closed path which it travels repeatedly, and to be removed from the closed path after passing through the gas sample a great number of times.

The foregoing detailed description is illustrative of several embodiments of the invention, and it is to be understood that additional embodiments thereof will be obvious to those skilled in the art. The embodiments described herein together with those additional embodiments are considered to be within the scope of the invention.

What is claimed is:

1. Apparatus for use in analyzing an absorbing medium comprising:
    a polarizing beamsplitter;
    mirrors positioned and oriented so as to provide a closed path for radiation, said closed path including at least two segments, a first segment incident upon said polarizing beamsplitter at the polarizing angle;
    confining means for maintaining a volume of the absorbing medium on the closed path;
    a pockels cell located on the closed path; and,
    timing means electrically connected to said pockels cell for applying voltage pulses to it for abruptly altering the direction of polarization of the radiation passing through said pockels cell.

2. The apparatus of claim 1 in which the closed path extends through said polarizing beamsplitter, said apparatus further comprising:
    a source of radiation positioned and oriented so as to direct radiation onto said polarizing beamsplitter at such an angle and position that the s-polarized component of the radiation is reflected from said polarizing beamsplitter along a segment of the closed path; and,
    a collector of radiation positioned and oriented to collect s-polarized radiation that is reflected from said polarizing beamsplitter after being incident upon said polarizing beamsplitter along said first segment.

3. The apparatus of claim 1 in which the closed path includes a vertex formed by reflection from said polarizing beamsplitter, and further comprising:
    a source of radiation positioned and oriented so as to direct radiation onto said polarizing beamsplitter at such an angle and position that the p-polarized component of the radiation is transmitted through said polarizing beamsplitter and emerges along a segment of the closed path; and, a collector of radiation positioned and oriented to collect p-polarized radiation that is transmitted through said polarizing beamsplitter after being incident upon said polarizing beamsplitter along said first segment.

4. Apparatus for causing radiation to repetitively travel a closed path and to repetitively pass through an absorbing medium maintained on the closed path, for introducing radiation to the closed path, and for removing radiation from the closed path, said apparatus comprising in combination:

a polarizing beamsplitter in which radiation linearly polarized perpendicular to the plane of incidence and incident upon said polarizing beamsplitter at the polarizing angle on a first path is reflected from said polarizing beamsplitter on a second path, and in which radiation linearly polarized parallel to the plane of incidence and incident upon said polarizing beamsplitter at the polarizing angle on the first path is transmitted through said polarizing beamsplitter and proceeds on a third path;

mirror means located and oriented to reflect radiation linearly polarized parallel to the plane of incidence repetitively on a closed path that passes through said polarizing beamsplitter and that coincides at least in part with the first and third paths;

confining means for maintaining a volume of the absorbing medium on the closed path;

a source of radiation linearly polarized perpendicular to the plane of incidence, positioned and oriented so as to direct radiation onto said polarizing beamsplitter at such an angle and position that the radiation linearly polarized perpendicular to the plane of incidence is reflected from said polarizing beamsplitter along the closed path;

pockels cell means on said closed path and selectively operable alternatively to rotate the direction of polarization of the radiation on said closed path by 90 degrees or to leave the direction of polarization of the radiation passing through it unchanged; and, timing means electrically connected to said pockels cell for applying voltage pulses to it for abruptly altering the direction of polarization of the radiation passing through said pockels cell, whereby as the radiation linearly polarized perpendicular to the plane of incidence is making its first circuit of the closed path, said pockels cell changes the direction of its polarization by 90 degrees so as to be parallel to the plane of incidence, and after that said pockels cell leaves the direction of polarization unchanged so that the radiation will continue to travel repetitively on the closed path until a desired number of circuits have been completed, after which said pockels cell once again changes the direction of polarization by 90 degrees so as to be perpendicular to the plane of incidence, which causes said polarizing beamsplitter to redirect the radiation from the closed path to the second path.

5. Apparatus for causing radiation to repetitively travel a closed path and to repetitively pass through an absorbing medium maintained on the closed path, for introducing radiation to the closed path, and for removing radiation from the closed path, said apparatus comprising in combination:

a polarizing beamsplitter in which radiation linearly polarized perpendicular to the plane of incidence and incident upon said polarizing beamsplitter at the polarizing angle on a first path is reflected from said polarizing beamsplitter on a second path, and in which radiation linearly polarized parallel to the plane of incidence and incident upon said polarizing beamsplitter at the polarizing angle on the first path is transmitted through said polarizing beamsplitter and proceeds on a third path;

mirror means located and oriented to reflect radiation linearly polarized perpendicular to the plane of incidence repetitively on a closed path that includes reflection from said polarizing beamsplitter and that coincides at least in part with the first and second paths;

confining means for maintaining a volume of the absorbing medium on the closed path;

a source of radiation linearly polarized parallel to the plane of incidence, positioned and oriented so as to direct radiation onto said polarizing beamsplitter at such an angle and position that the radiation linearly polarized parallel to the plane of incidence is transmitted through said polarizing beamsplitter and emerges along the closed path;

pockels cell means located on said closed path and selectively operable alternatively to rotate the direction of polarization of the radiation on said closed path by 90 degrees or to leave the direction of polarization of the radiation passing through it unchanged; and, timing means electrically connected to said pockels cell for applying voltage pulses to it for abruptly altering the direction of polarization of the radiation passing through said pockels cell, whereby as the radiation linearly polarized parallel to the plane of incidence is making its first circuit of the closed path, said pockels cell changes the direction of its polarization by 90 degrees so as to be perpendicular to the plane of incidence, and after that said pockels cell leaves the direction of polarization unchanged so that the radiation will continue to travel repetitively on the closed path until a desired number of circuits have been completed, after which said pockels cell once again changes the direction of polarization by 90 degrees so as to be parallel to the plane of incidence, which causes said polarizing beamsplitter to redirect the radiation from the closed path to the third path.

6. A method for causing radiation to repetitively travel a closed path and to repetitively pass through an absorbing medium maintained on the closed path, for introducing radiation to the closed path, and for removing radiation from the closed path, said method comprising the steps of:

directing a beam of unpolarized radiation along a first path at a polarizing beamsplitter so that the beam is incident at the polarizing angle, whereby the s-component of the beam is reflected on a second path;

placing a first mirror on the second path so that the s-component will be reflected back along the second path;

placing a pockels cell in the second path between the polarizing beamsplitter and the first mirror;

temporarily applying a first signal to the pockels cell that causes the s-polarized radiation to become p-polarized after having passed twice through the pockels cell, whereby the radiation returning from the first mirror, after passing a second time through the pockels cell, again is incident at the polarizing angle on the polarizing beamsplitter but now with p-polarization, whereby the radiation is transmitted through the polarizing beamsplitter and emerges along a third path;

placing a second mirror along the third path to reflect the emerging radiation back upon itself, whereby said second and third paths together constitute the closed path;

maintaining a volume of an absorbing medium along a portion of the closed path, whereby radiation travelling on the closed path passes repeatedly through the volume of absorbing medium;

temporarily applying a second signal to the pockels cell that allows radiation to pass through it with no change in the angle of polarization, whereby the p-polarized radiation is reflected back and forth many times between the first mirror and the second mirror along the second and third paths repetitively while maintaining its p polarization; and, temporarily applying the first signal to the pockels cell whereby radiation emerging from the polarizing beamsplitter on the second path returns after passing twice through the pockels cell with its polarization altered from p to s, whereby the returning radiation is reflected along the first path by the polarizing beamsplitter.

7. A method for causing radiation to repetitively travel a closed path and to repetitively pass through an absorbing medium maintained on the closed path, for introducing radiation to the closed path, and for removing radiation from the closed path, said method comprising the steps of:

directing a beam of unpolarized radiation along a first path at a polarizing beamsplitter so that the beam is incident at the polarizing angle, whereby the s component of the beam is reflected on a second path;

using mirrors to define a closed path that passes once through the polarizing beamsplitter and that includes a segment that coincides with said second path;

placing a pockels cell in the closed path;

temporarily applying a first signal to the pockels cell that causes the s-polarized radiation that passes through it to become p-polarized, whereby the p-polarized radiation continues on the closed path and is transmitted through the polarizing beamsplitter to emerge on the segment that coincides with said second path, thereby starting another circuit around the closed path;

temporarily applying a second signal to the pockels cell that allows radiation to pass through it with no change in the angle polarization, whereby the p-polarized radiation repetitively circulates on the closed path;

maintaining a volume of an absorbing medium along a portion of the closed path, whereby radiation travelling on the closed path passes repeatedly through the volume of absorbing medium;

temporarily applying said first signal to the pockels cell, whereby as the circulating p-polarized radiation passes through the pockels cell, its polarization is changed from p to s, whereby, as s-polarized radiation it is reflected from the polarizing beamsplitter along a third path thereby leaving the closed path.

8. A method for causing radiation to repetitively travel a closed path, for introducing radiation to the closed path, and for removing radiation from the closed path, said method comprising the steps of:

directing a beam of unpolarized radiation along a first path at a polarizing beamsplitter so that the beam is incident at the polarizing angle, whereby the p component of the beam is transmitted by the polarizing beamsplitter and emerges from the polarizing beamsplitter on a second path;

placing a first mirror on the second path so as to reflect the radiation back along the second path;

placing a pockels cell in the second path between the polarizing beamsplitter and the first mirror;

temporarily applying a first signal to the pockels cell that causes p-polarized radiation to become s-polarized after having passed twice through the pockels cell, whereby the p component of the beam, after emerging from the polarizing beamsplitter, passes through the pockels cell a first time, is reflected from the first mirror, and passes through the pockels cell a second time thereby becoming s-polarized before returning to the place where it emerged from the polarizing beamsplitter, and whereby upon impinging on the polarizing beamsplitter is reflected along a third path;

placing a second mirror along the third path to reflect the radiation back upon itself, whereby the second and third paths together constitute the closed path;

maintaining a volume of an absorbing medium along a portion of the closed path, whereby radiation travelling on the closed path passes repeatedly through the volume of absorbing medium;

temporarily applying a second signal to the pockels cell that allows radiation to pass through it with no change in the angle of polarization, whereby the s-polarized radiation is reflected back and forth many times between the first mirror and the second mirror along the second and third paths repetitively, while maintaining its s-polarization; and, temporarily applying said first signal to the pockels cell whereby radiation travelling on the second path from the first mirror towards the polarizing beamsplitter will have its polarization altered from s to p, whereby the resulting p-polarized radiation is transmitted through the polarizing beamsplitter and emerges along the first path.

9. A method for causing radiation to repetitively travel a closed path and to repetitively pass through an absorbing medium maintained on the closed path, for introducing radiation to the closed path, and for removing radiation from the closed path, said method comprising the steps of:

directing a beam of unpolarized radiation at a polarizing beamsplitter so that the beam is incident at the polarizing angle, whereby the p component of the beam is transmitted through the polarizing beamsplitter and emerges from a first surface of it on a first path;

using mirrors and said first surface of the polarizing beamsplitter to define a closed path, a segment of which coincides with said first path;

placing a pockels cell in the closed path;

temporarily applying a first signal to the pockels cell that causes the p-polarized radiation that has emerged from the polarizing beamsplitter and that passes through it to become s-polarized, whereby the s-polarized radiation continues on the closed path, eventually arriving at the place on the first surface of the polarizing beamsplitter at which it emerged;

temporarily applying a second signal to the pockels cell that allows radiation to pass through it with no change in the angle of polarization, whereby the s-polarized radiation repetitively circulates on the closed path;

maintaining a volume of an absorbing medium along a portion of the closed path, whereby radiation travelling on the closed path passes repeatedly through the volume of absorbing medium; and, temporarily applying said first signal to the pockels cell, whereby as the circulating s-polarized radiation passes through the pockels cell, its polarization is changed from s to p, whereby, as p-polarized radiation it is transmitted through the polarizing beamsplitter thereby leaving the closed path.

* * * * *